United States Patent
Riehlman et al.

(10) Patent No.: US 12,259,355 B2
(45) Date of Patent: *Mar. 25, 2025

(54) MICROCHIP CAPILLARY ELECTROPHORESIS ASSAYS AND REAGENTS

(71) Applicant: Regeneron Pharmaceuticals, Inc., Tarrytown, NY (US)

(72) Inventors: Timothy Riehlman, Tarrytown, NY (US); Gabriel Carreau, Tarrytown, NY (US); Jeffrey Schneiderheinze, Tarrytown, NY (US); Nicole M. Nall, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 888 days.

This patent is subject to a terminal disclaimer.

(21) Appl. No.: 17/368,377

(22) Filed: Jul. 6, 2021

(65) Prior Publication Data
US 2021/0333235 A1 Oct. 28, 2021

Related U.S. Application Data

(63) Continuation-in-part of application No. 17/335,756, filed on Jun. 1, 2021, and a continuation-in-part of application No. 16/355,050, filed on Mar. 15, 2019, now Pat. No. 11,054,389, said application No. 17/335,756 is a continuation-in-part of application No. 16/355,050, filed on Mar. 15, 2019, now Pat. No. 11,054,389.

(60) Provisional application No. 62/644,933, filed on Mar. 19, 2018.

(51) Int. Cl.
G01N 27/447 (2006.01)

(52) U.S. Cl.
CPC . *G01N 27/44726* (2013.01); *G01N 27/44791* (2013.01)

(58) Field of Classification Search
None
See application file for complete search history.

(56) References Cited

U.S. PATENT DOCUMENTS

| | | | |
|---|---|---|---|
| 6,924,372 B2 | 8/2005 | Czerney et al. |
| 6,927,004 B2 | 8/2005 | Eurlings et al. |
| 7,087,411 B2 | 8/2006 | Daly et al. |
| 7,279,159 B2 | 10/2007 | Daly et al. |
| 7,378,396 B2 | 5/2008 | Hazen et al. |
| 7,582,298 B2 | 9/2009 | Stevens et al. |
| 7,879,984 B2 | 2/2011 | Martin et al. |
| 8,043,617 B2 | 10/2011 | Stevens et al. |
| 8,062,640 B2 | 11/2011 | Sleeman et al. |
| 8,309,088 B2 | 11/2012 | MacDonald et al. |
| 8,586,713 B2 | 11/2013 | Davis et al. |
| 8,735,095 B2 | 5/2014 | Martin et al. |
| 8,871,209 B2 | 10/2014 | Stitt et al. |
| 8,945,559 B2 | 2/2015 | Dix et al. |
| 9,018,356 B2 | 4/2015 | Sleeman et al. |
| 9,079,948 B2 | 7/2015 | Orengo et al. |
| 9,132,192 B2 | 9/2015 | Daly et al. |
| 9,173,880 B2 | 11/2015 | Dix et al. |
| 9,228,014 B2 | 1/2016 | Classon et al. |
| 9,260,515 B2 | 2/2016 | Stitt et al. |
| 9,265,827 B2 | 2/2016 | Wiegand et al. |
| 9,302,015 B2 | 4/2016 | Papadopoulos et al. |
| 9,353,176 B2 | 5/2016 | MacDonald et al. |
| 9,402,898 B2 | 8/2016 | Walsh et al. |
| 9,447,173 B2 | 9/2016 | Gurnett-Bander et al. |
| 9,453,072 B2 | 9/2016 | Murphy et al. |
| 9,475,875 B2 | 10/2016 | Kirshner et al. |
| 9,540,449 B2 | 1/2017 | Yancopoulos et al. |
| 9,587,029 B2 | 3/2017 | Okamoto et al. |
| 9,612,247 B2 | 4/2017 | Chumsae et al. |
| 9,637,535 B2 | 5/2017 | Murphy et al. |
| 9,657,099 B2 | 5/2017 | Okamoto et al. |
| 9,657,102 B2 | 5/2017 | Smith et al. |
| 9,718,872 B2 | 8/2017 | Kyratsous et al. |
| 9,771,414 B2 | 9/2017 | Kyratsous et al. |
| 9,795,121 B2 | 10/2017 | Hu et al. |
| 9,938,345 B2 | 4/2018 | Papadopoulos et al. |
| 9,987,500 B2 | 6/2018 | Papadopoulos et al. |
| 11,054,389 B2* | 7/2021 | Riehlman .......... G01N 33/6815 |
| 2009/0233309 A1* | 9/2009 | Fischer .............. C12N 15/1003 435/6.1 |
| 2012/0234678 A1 | 9/2012 | Diller et al. |
| 2014/0271681 A1 | 9/2014 | Martin et al. |
| 2015/0104806 A1 | 4/2015 | Alessi et al. |
| 2015/0266966 A1 | 9/2015 | Smith et al. |
| 2015/0343040 A1 | 12/2015 | Davey |
| 2016/0017029 A1 | 1/2016 | Walsh et al. |
| 2019/0285580 A1 | 9/2019 | Riehlman et al. |
| 2021/0293749 A1 | 9/2021 | Riehlman et al. |

FOREIGN PATENT DOCUMENTS

| | | |
|---|---|---|
| JP | 2003-114216 A | 4/2003 |
| JP | 2005-534616 A | 11/2005 |

(Continued)

OTHER PUBLICATIONS

Japanese Office Action for Application No. 2020-542113, dated May 18, 2022, 9 pages.

(Continued)

*Primary Examiner* — J. Christopher Ball
*Assistant Examiner* — John C Ball
(74) *Attorney, Agent, or Firm* — McCarter & English, LLP

(57) ABSTRACT

Microchip Capillary Electrophoresis (MCE) assays and reagents to assess purity and to identify impurities in protein drug product samples are provided. Methods for analyzing analytes in a protein drug sample are provided.

24 Claims, 1 Drawing Sheet

(56) References Cited

FOREIGN PATENT DOCUMENTS

| JP | 2007-520688 | A  | 7/2007 |
|----|-------------|----|--------|
| JP | 2010-518386 | A  | 5/2010 |
| JP | 2011-2460   | A  | 1/2011 |
| JP | 2012-507499 | A  | 3/2012 |
| TW | 202004178   | A  | 1/2020 |
| WO | 2005/036153 | A1 | 4/2005 |
| WO | 2006/020498 | A2 | 2/2006 |
| WO | 2012/087972 | A2 | 6/2012 |
| WO | 2013/087914 | A1 | 6/2013 |
| WO | 2014/055936 | A1 | 4/2014 |
| WO | 2014/116596 | A1 | 7/2014 |
| WO | 2019/182901 | A1 | 9/2019 |

OTHER PUBLICATIONS

An et al., Automated high-throughput dense matrix protein folding screen using a liquid handling robot combined with microfluidic capillary electrophoresis. Protein Expr Purif. Apr. 2016;120:138-47.
International Search Report and Written Opinion received for PCT Patent Application No. PCT/US2022/031738, dated Sep. 19, 2022, 16 pages.
Ashkenazi et al., Protection against endotoxic shock by a tumor necrosis factor receptor immunoadhesin. Proc Natl Acad Sci U S A. Dec. 1, 1991;88(23):10535-9.
Byrn et al., Biological properties of a CD4 immunoadhesin. Nature. Apr. 12, 1990;344(6267):667-70.
Ouimet et al., Advances in capillary electrophoresis and the implications for drug discovery. Expert Opin Drug Discov. Feb. 2017;12(2):213-224.
Sinclair et al., Improved retention of heme with increased resolution of microsomal proteins in polyacrylamide gel electrophoresis. Anal Biochem. Jul. 1, 1981;114(2):316-21.
Westermann et al., The alpha and gamma subunits of initiation factor eIF-2 can be cross-linked to 18S ribosomal RNA within the quaternary initiation complex, eIF-2.Met-IRNAf.GDPCP.small ribosomal subunit. Nucleic Acids Res. Jul. 25, 1980;8(14):3065-71.
International Preliminary Report on Patentability for Application No. PCT/US2019/022525, dated Oct. 1, 2020, 10 pages.
International Search Report and Written Opinion received for PCT Patent Application No. PCT/US19/022525, dated Aug. 19, 2019, 14 pages.
Invitation to Pay Additional Fees for Application No. PCT/US2019/022525, dated Jun. 24, 2019, 15 pages.

\* cited by examiner

MICROCHIP CAPILLARY ELECTROPHORESIS ASSAYS AND REAGENTS

CROSS-REFERENCE TO RELATED APPLICATIONS

This application is a continuation-in-part application of U.S. patent application Ser. No. 17/335,756 filed on Jun. 1, 2021, which is a continuation-in-part application of U.S. patent application Ser. No. 16/355,050 filed on Mar. 15, 2019, which claims benefit of and priority to U.S. Provisional Application No. 62/644,933 filed on Mar. 19, 2018 This application also is a continuation-in-part application of U.S. patent application Ser. No. 16/355,050 filed on Mar. 15, 2019, which claims benefit of and priority to U.S. Provisional Application No. 62/644,933 filed on Mar. 19, 2018. Each of these applications are incorporated by reference in its entirety.

TECHNICAL FIELD OF THE INVENTION

Aspects of the invention are generally directed to the field of capillary electrophoresis, in particular to microchip capillary electrophoresis.

BACKGROUND OF THE INVENTION

Implementation of robust, reproducible, user-friendly technology is critical to meet the testing demands of biological products in today's Quality Control (QC) laboratories. Upgrades in technology are necessary to facilitate increased output, while continuing to generate quality analytical data and attempting to minimize the number of invalid test results and instrument-related investigations. While electrophoresis has historically been used in QC for product purity and fragmentation analysis, the methodology has transitioned from gel-based, to capillary-based, and more recently, to the microchip. Microchip Capillary Electrophoresis (MCE) allows for dramatically reduced sample analysis times, while maintaining the performance and reproducibility standards required for QC analysis (Ouimet, C., et al., *Expert Opin Drug Discov.*, 12(2): 213-224 (2017)).

Although MCE has emerged as a promising technique with growing use in the pharmaceutical industry for characterizing biopharmaceuticals, quality control, and for drug discovery, it can be prone to assay interferences.

Thus, it is an object of the invention to provide improved MCE assays and compositions that reduce assay interferences.

It is another object of the invention to provide MCE assays and compositions for improving detection of impurities in a protein drug product.

SUMMARY OF THE INVENTION

MCE assays and reagents to assess purity and to identify impurities in protein drug product samples are provided. Methods for analyzing analytes in a protein drug sample are provided. Preferred protein drugs include but are not limited to recombinant proteins such as antibodies and antigen binding fragments thereof, and fusion proteins. The assays employ MCE techniques to separate, identify, and quantify protein product and impurities in the protein product. Impurities include, but are not limited to protein aggregates, protein fragments, protein multimers, and assay contaminants. Reducing and non-reducing buffers are also provided.

In some embodiments, the MCE assays and reagents provided herein may be used in the analysis and purity testing of Anti-SARS-CoV-2 products, such as therapeutic protein products including REGEN-COV™ (casirivimab and imdevimab).

An embodiment provides a non-reducing aqueous electrophoresis sample buffer containing an alkylating agent such as 2-iodoacetamide (IAM), iodoacetic acid (IAA), or N-ethylmaleimide (NEM). In one embodiment, the non-reducing aqueous electrophoresis sample buffer contains an alkylating agent, 155 to 175 mM 2-iodoacetamide; 0.50 to 1.5% lithium dodecyl sulfate; and 65 to 95 mM sodium phosphate, wherein the aqueous electrophoresis sample buffer has a pH of less than 7. In an embodiment, the pH of the buffer is 6. In another embodiment, the aqueous buffer contains 166 mM 2-iodoacetamide, 0.81% lithium dodecyl sulfate, and 81 mM sodium phosphate.

In another embodiment, the non-reducing aqueous electrophoresis sample buffer contains an alkylating agent, for example 50 to 250 or 155 to 200 or 155 to 250 mM 2-iodoacetamide; 0.50 to 1.5% lithium dodecyl sulfate; and 40 to 80 mM or 50 to 70 mM sodium phosphate, wherein the aqueous electrophoresis sample buffer has a pH of less than or equal to 8. In an embodiment, the pH of the buffer is 8. In yet another embodiment, the aqueous buffer contains 200 mM 2-iodoacetamide, 1.2% lithium dodecyl sulfate, and 60 mM sodium phosphate.

In another embodiment, the non-reducing aqueous electrophoresis sample buffer contains an alkylating agent, for example 155 to 200 mM 2-iodoacetamide; 0.50 to 1.5% lithium dodecyl sulfate; and 50 to 70 mM sodium phosphate, wherein the aqueous electrophoresis sample buffer has a pH 8 or less. In an embodiment, the pH of the buffer is 6. In yet another embodiment, the aqueous buffer contains 200 mM 2-iodoacetamide, 1.2% lithium dodecyl sulfate, and 60 mM sodium phosphate.

A reducing buffer is also provided. In one embodiment, the reducing buffer is an aqueous electrophoresis sample buffer containing 0.5 to 1.5% lithium dodecyl sulfate, 55 to 85 mM sodium phosphate, and a reducing agent, wherein the aqueous electrophoresis sample buffer has a pH greater than 8. In an embodiment, the pH of the buffer is 9. In one embodiment, the reducing buffer contains 135 to 155 mM dithiothreitol. Still another embodiment provides a reducing buffer containing 0.69% lithium dodecyl sulfate, 69 mM sodium phosphate, and 142 mM dithiothreitol.

In another embodiment, the reducing buffer is an aqueous electrophoresis sample buffer containing 0.5 to 1.5% lithium dodecyl sulfate, 45 to 85 mM sodium phosphate, and a reducing agent, wherein the aqueous electrophoresis sample buffer has a pH of 8 or greater. In an embodiment, the pH of the buffer is 8. In one embodiment, the reducing buffer contains 80 to 155 mM dithiothreitol. Still another embodiment provides a reducing buffer containing 1.2% lithium dodecyl sulfate, 60 mM sodium phosphate, and 80 mM dithiothreitol.

HEPES based buffers can also be used with the disclosed methods. One embodiment provides a non-reducing HEPES based aqueous electrophoresis sample buffer containing an alkylating agent, for example 55 to 75 mM 2-iodoacetamide; 0.1 to 1.0% lithium dodecyl sulfate; 5 to 85 mM HEPES, and 5 to 115 mM sodium chloride, wherein the aqueous electrophoresis sample buffer has a pH of less than 9. In another embodiment, the pH of the buffer is 8. In still another embodiment, the aqueous buffer contains 66.4 mM 2-iodoacetamide, 0.32% lithium dodecyl sulfate, 16.2 mM HEPES, and 48.6 mM sodium chloride.

Another embodiment provides a reducing HEPES based aqueous electrophoresis sample buffer containing 0.05 to 0.75% lithium dodecyl sulfate, 5 mM to 115 mM sodium chloride, 5 mM to 115 mM HEPES, and a reducing agent, wherein the aqueous electrophoresis sample buffer has a pH greater than 7. In an embodiment, the pH of the buffer is 8. In one embodiment, the reducing buffer contains 35 to 50 mM dithiothreitol. Still another embodiment provides a reducing buffer containing 0.28% lithium dodecyl sulfate, 41.5 mM sodium chloride, 13.8 mM HEPES, and 42.5 mM dithiothreitol.

One embodiment provides a non-reducing MCE method for identifying contaminants or impurities in a protein drug sample including the steps of adding the protein sample to a non-reducing buffer discussed above to form a buffered protein drug sample. The buffered protein drug sample is heated to between 65 to 85° C. for 5 to 15 minutes to form a denatured buffered protein drug sample. In an embodiment, the buffered protein drug sample is heated to 70° C. for 10 min.

In another embodiment, a non-reducing MCE method for identifying contaminants or impurities in a protein drug sample includes the steps of adding the protein sample to a non-reducing buffer discussed above to form a buffered protein drug sample. The buffered protein drug sample is heated to between 50 to 72° C. for 5 to 15 minutes to form a denatured buffered protein drug sample. Alternately, the buffered protein drug sample is heated to between 45 to 75° C. for 5 to 15 minutes to form a denatured buffered protein drug sample. In an embodiment, the buffered protein drug sample is heated to 60° C.-65° C. for 10 min. In another embodiment, the buffered protein drug sample is heated to 63° C. for 10 min. In another embodiment, the buffered protein drug sample is heated to 60° C. for 10 min.

In some embodiments, the protein drug sample is mixed with a detectable label and heated at 30 to 40° C. for 20 to 40 minutes or for 10 to 40 minutes to form a denatured labeled protein drug sample. In other embodiments, the protein drug sample is mixed with a detectable label and heated at 30 to 40° C. for 15 minutes to form a denatured labeled protein drug sample. A detectable label includes, but is not limited to Dyomics DY-631 NHS Ester. In some embodiments, the label is diluted by MilliQ purified water, and in other embodiments the label is diluted in a sodium phosphate buffer. In some examples, the detectable label is reconstituted with dimethyl sulfoxide (DMSO) followed by dilution with 200 mM Sodium Phosphate pH 7.2 buffer. Other detectable labels can be used, including other dyes, fluorophores, chromophores, mass tags, quantum dots and the like and those disclosed in U.S. Pat. No. 6,924,372. In an embodiment, the protein drug sample with added label is heated to 35° C. for 30 minutes. In another embodiment, the protein drug sample with added label is heated to 35° C. for 15 minutes. Excess label is optionally removed from the sample, for example by using a spin filter. In still another embodiment, excess label is not quenched. In still another embodiment, excess label is not removed.

The denatured labeled protein drug product is diluted and subjected to MCE to separate the diluted protein drug sample on a microchip capillary electrophoresis system to produce an electropherogram. In one embodiment the final concentration of a sample starting at 0.5 mg/ml that is then injected over the microchip is 9 µg/ml to MCE. In another embodiment, the final concentration of a sample starting at 0.2 mg/ml that is then injected over the microchip is 3.6 µg/ml to MCE. The electropherogram contains peaks corresponding to the protein drug product and impurities. The method concludes by identifying peaks in the electropherogram corresponding to the protein drug product, contaminants, and/or impurities.

Another embodiment provides a reducing MCE method for identifying contaminants or impurities in a protein drug sample. The method begins by adding the protein sample to any one of the reducing buffers described above to form a buffered protein drug sample. The buffered protein drug sample is denatured by heating the buffered protein drug sample to 65 to 85° C., preferably to 75° C. for 10 minutes to form a denatured protein drug sample. The protein drug sample is mixed with a detectable label and heated at 30 to 40° C. for 20 to 40 minutes to form a denatured labeled protein drug sample. In an embodiment, the protein drug sample with added label is heated to 35° C. for 30 minutes.

In other embodiments, the buffered protein drug sample is denatured by heating the buffered protein drug sample to 50-72° C., preferably to 60° C. for 10 minutes to form a denatured protein drug sample. For example, the protein drug sample is mixed with a detectable label and heated at 30 to 40° C. for 15 minutes to form a denatured labeled protein drug sample. In another embodiment, the protein drug sample with added label is heated to 35° C. for 15 minutes.

Excess label is optionally removed from the sample, for example by using a spin filter. In still another embodiment, excess label is not quenched. In still another embodiment, excess label is not removed. An exemplary detectable label includes, but is not limited to Dyomics DY-631 NHS Ester. Other detectable labels that can be used include other dyes, fluorophores, chromophores, mass tags, quantum dots and the like and those disclosed in U.S. Pat. No. 6,924,372.

In one embodiment, the established assay range for sample concentration is from 0.4 mg/ml to 0.6 mg/ml, corresponding to a final concentration being analyzed of about 7 µg/ml to 11 µg/ml which is subjected to MCE analysis on a microchip capillary electrophoresis system to produce an electropherogram. In another embodiment, the established assay range for sample concentration is from 0.2 mg/ml to 0.6 mg/ml, corresponding to a final concentration being analyzed of about 3.6 µg/ml to 11 µg/ml. The method concludes by identifying peaks in the electropherogram corresponding to the protein drug product, contaminants, and/or impurities.

DETAILED DESCRIPTION OF THE INVENTION

I. Definitions

Figure 1A:
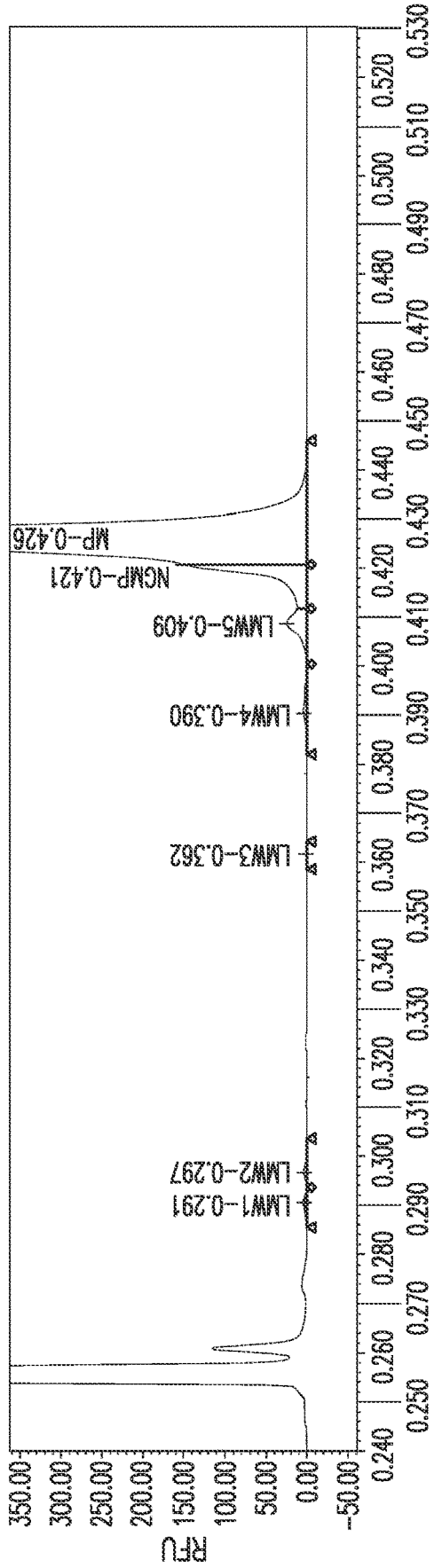
FIG. 1A shows an electropherogram of a typical non-reduced sample analysis.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

"Protein" refers to a molecule comprising two or more amino acid residues joined to each other by a peptide bond. Protein includes polypeptides and peptides and may also include modifications such as glycosylation, lipid attachment, sulfation, gamma-carboxylation of glutamic acid residues, alkylation, hydroxylation and ADP-ribosylation. Proteins can be of scientific or commercial interest, including protein-based drugs, and proteins include, among other things, enzymes, ligands, receptors, antibodies and chimeric or fusion proteins. Proteins are produced by various types of recombinant cells using well-known cell culture methods, and are generally introduced into the cell by genetic engineering techniques (e.g., such as a sequence encoding a chimeric protein, or a codon-optimized sequence, an intronless sequence, etc.) where it may reside as an episome or be integrated into the genome of the cell.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyterminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in U.S. Pat. No. 8,586,713.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., Proc. Natl. Acad. Sci USA, 88: 10535 (1991); Byrn et al., Nature 344:677 (1990); and Hollenbaugh et al., "Construction of Immunoglobulin Fusion Proteins", in Current Protocols in Immunology, Suppl. 4, pages 10.19.1-10.19.11 (1992). "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein comprises two or more distinct receptor chains that bind to a one or more ligand(s). For example, an Fc-fusion protein is a trap, such as for example an IL-1 trap or VEGF trap.

The term "MCE" or "Microchip Capillary Electrophoresis" refers to microchip-based capillary electrophoresis (CE) separation of analytes.

II. MCE Assays and Buffers

Methods for analyzing analytes in a protein drug sample are provided. Protein drugs include, but are not limited to antibodies and antigen binding fragments thereof, fusion proteins, and recombinant proteins. The assays employ MCE techniques to separate, identify, and quantify protein product and impurities in the protein product. Impurities include, but are not limited to protein aggregates, protein fragments, protein multimers, and assay contaminants. Reducing and non-reducing buffers are also provided.

Microchip Capillary Electrophoresis (MCE) provides analysis of protein purity and impurities suitable for in-process testing, lot release, and stability indication. Protein samples, such as casirivimab and imdevimab, were prepared by denaturing the sample through heating and addition of lithium dodecyl sulfate (LDS) with either an alkylating agent (non-reduced) or a reducing agent (reduced). Not intending to be bound by theory, this produces linear negatively charged protein-LDS polypeptide chains, which are then incubated with an amine ester dye to covalently label any free amine groups. Labeled samples may be injected onto a microchip where the application of a current separates the sample components according to mass to charge ratio. Detection can be performed by laser-induced fluorescence, producing an electropherogram. Analysis of the electropherogram provides the relative purity of the sample compared to the impurities present.

A. Buffers

1. Non-Reducing Buffers

One embodiment provides a non-reducing aqueous electrophoresis sample buffer containing 155 to 200 mM of an alkylating agent for example 2-iodoacetamide; 0.50 to 1.5% lithium dodecyl sulfate; and 60 to 95 mM sodium phosphate, wherein the aqueous electrophoresis sample buffer has a pH of less than 7. In an embodiment, the pH of the buffer is 6. In another embodiment, the aqueous buffer contains 166 mM 2-iodoacetamide, 0.81% lithium dodecyl sulfate, and 81 mM sodium phosphate.

Another embodiment provides a non-reducing aqueous electrophoresis sample buffer containing 155 to 200 mM of an alkylating agent; 0.50 to 1.5% lithium dodecyl sulfate; and 60 to 95 mM sodium phosphate, wherein the aqueous electrophoresis sample buffer has a pH of less than or equal to 8. In another embodiment, the pH of the buffer is 8. In another embodiment, the aqueous buffer contains 200 mM 2-iodoacetamide, 1.2% lithium dodecyl sulfate, and 60 mM sodium phosphate.

Another embodiment provides a non-reducing aqueous electrophoresis sample buffer containing 155 to 200 mM of an alkylating agent; 0.50 to 1.5% lithium dodecyl sulfate; and 60 to 95 mM sodium phosphate, wherein the aqueous electrophoresis sample buffer has a pH of less than 8. In another embodiment, the pH of the buffer is 6. In another embodiment, the aqueous buffer contains 200 mM 2-iodoacetamide, 1.2% lithium dodecyl sulfate, and 60 mM sodium phosphate.

2. Reducing Buffers

A reducing buffer is also provided. In one embodiment, the reducing buffer is an aqueous electrophoresis sample buffer containing 0.5 to 1.5% lithium dodecyl sulfate, 65 to 95 mM sodium phosphate, and a reducing agent, wherein the aqueous electrophoresis sample buffer has a pH greater than 8. In another embodiment, the reducing buffer contains 0.5 to 1.5% lithium dodecyl sulfate, 45 to 95 mM sodium phosphate, and a reducing agent, and the aqueous electrophoresis sample buffer has a pH of 8 or greater. In an embodiment, the pH of the buffer is 9. In another embodiment, the pH of the buffer is 8.

Reducing agents are known in the art. Exemplary reducing agents include but are not limited to dithiothreitol (DTT, CAS 3483-12-3), beta-mercaptoethanol (BME, 2BME, 2-ME, b-mer, CAS 60-24-2), 2-aminoethanethiol (2-MEA-HCl, also called cysteamine-HCl, CAS 156-57-0), Tris(2-carboxyethyl) phosphine hydrochloride, (TCEP, CAS 5961-85-3), cysteine hydrochloride (Cys-HCl, CAS 52-89-1), or 2-mercaptoethanesulfonic acid sodium salt (MESNA). Other methods for reducing protein bonds are known in the art, such as an immobilized reductant column which contains resin to which a thiol-based reducing agent has been immobilized to enable the solid-phase reduction of peptide and protein disulfide bonds. Additional reducing agents suitable for cleaving disulfide bonds are also envisioned.

In one embodiment, the reducing buffer contains 135 to 155 mM dithiothreitol. In another embodiment, the reducing buffer contains 80 to 155 mM dithiothreitol.

Still another embodiment provides a reducing buffer containing 0.69% lithium dodecyl sulfate, 69 mM sodium phosphate, and 142 mM dithiothreitol, or 1.2% lithium dodecyl sulfate, 60 mM sodium phosphate, and 80 mM dithiothreitol.

3. HEPES Based Non-Reducing Buffers

HEPES based buffers can also be used with the disclosed methods. One embodiment provides a non-reducing HEPES based aqueous electrophoresis sample buffer containing an alkylating agent, for example 55 to 75 mM 2-iodoacetamide; 0.1 to 1.0% lithium dodecyl sulfate; 5 to 85 mM HEPES, and 5 to 115 mM sodium chloride, wherein the aqueous electrophoresis sample buffer has a pH of less than 9. In an embodiment, the pH of the buffer is 8. In another embodiment, the aqueous buffer contains 66.4 mM 2-iodoacetamide, 0.32% lithium dodecyl sulfate, 16.2 mM HEPES, and 48.6 mM sodium chloride.

4. HEPES Based Reducing Buffers

Another embodiment provides a reducing HEPES based aqueous electrophoresis sample buffer containing 0.05 to 0.75% lithium dodecyl sulfate, 5 mM to 115 mM sodium chloride, 5 mM to 115 mM HEPES, and a reducing agent, wherein the aqueous electrophoresis sample buffer has a pH greater than 7. In an embodiment, the pH of the buffer is 8. In one embodiment, the reducing buffer contains 35 to 50 mM dithiothreitol. Still another embodiment provides a reducing buffer containing 0.28% lithium dodecyl sulfate, 41.5 mM sodium chloride, 13.8 mM HEPES, and 42.5 mM dithiothreitol.

B. Assays

1. Non-Reducing Assays

One embodiment provides a non-reducing MCE method for identifying contaminants or impurities in a protein drug sample, the method including the steps of adding the protein sample to a non-reducing buffer discussed above to form a buffered protein drug sample. The buffered protein drug sample is heated to between 50 to 85° C. for 5 to 15 minutes to form a denatured buffered protein drug sample. In an embodiment, the buffered protein drug sample is heated to 75° C. for 10 min. In another embodiment, the buffered protein drug sample is heated to between 45 to 75° C. for 5 to 15 minutes to form a denatured buffered protein drug sample. In another preferred embodiment, the buffered protein drug sample is heated to 60° C. for 10 min. In yet another preferred embodiment, the buffered protein drug sample is heated to 63° C. for 10 min.

A detectable label is prepared to vendor recommendations in dimethyl sulfoxide (DMSO). Subsequent dilutions are prepared per vendor recommendations in MilliQ. In other embodiments, the label is prepared by dilution in 200 mM sodium phosphate pH 7.2. In some embodiments, the label is diluted to a 5 µM solution. In other embodiments, the label is diluted to a 16 µM solution. The diluted label is then added to the denatured buffered protein drug sample and heated at 30 to 40° C. for 10 to 40 minutes to form a denatured labeled protein drug sample. In another embodiment, a detectable label is then added to the denatured buffered protein drug sample and heated at 30 to 40° C. for 15 minutes to form a denatured labeled protein drug sample. In an embodiment, the denatured protein drug sample with added label is heated to 35° C. for 30 minutes. In another preferred embodiment, the denatured protein drug sample with added label is heated to 35° C. for 15 minutes. Excess label is optionally removed from the sample, for example by using a spin filter. In still another embodiment, excess label is not quenched. In still another embodiment, excess label is not removed.

A preferred detectable label includes, but is not limited to Dyomics DY-631 NHS Ester. Other detectable labels can be used include other dyes, fluorophores, chromophores, mass tags, quantum dots and the like and those disclosed in U.S. Pat. No. 6,924,372.

The denatured labeled protein drug product is diluted and subjected to MCE to separate the diluted protein drug sample on a microchip capillary electrophoresis system to produce an electropherogram. In one embodiment the final concentration of a sample starting at 0.5 mg/ml that is then injected over the microchip is 9 µg/ml to MCE. In another embodiment, the sample starting concentration is 0.2 mg/ml. The electropherogram contains peaks corresponding to the protein drug product and impurities. The method concludes by identifying peaks in the electropherogram corresponding to contaminants or impurities.

2. Reducing Assays

Another embodiment provides a reducing MCE method for identifying contaminants or impurities in a protein drug sample. The method begins by adding the protein drug sample to any one of the reducing buffers described above to form a buffered protein drug sample. The buffered protein drug sample is denatured by heating the buffered protein drug sample to 65 to 85° C., preferably to 75° C. for 10 minutes to form a denatured protein drug sample. In another embodiment, the buffered protein drug sample is denatured by heating the buffered protein drug sample to 50 to 72° C., or 45 to 75° C., or preferably to 60° C. for 10 minutes to form a denatured protein drug sample. In yet another preferred embodiment, the buffered protein drug sample is heated to 63° C. for 10 min. The temperature needed to denature the target protein drug sample may be changed according to the structure of the target protein drug sample.

The protein drug sample with added label is then heated at 30 to 40° C. for 20 to 40 minutes or for 10 to 20 or for 10 to 40 minutes to form a denatured labeled protein drug sample. In an embodiment, the protein drug product sample with added label is heated to 35° C. for 30 minutes. In another preferred embodiment, the protein drug product sample with added label is heated to 35° C. for 15 minutes. Excess label is optionally removed from the sample, for example by using a spin filter. In still another embodiment, excess label is not quenched. In still another embodiment, excess label is not removed. A preferred detectable label includes, but is not limited to Dyomics DY-631 NHS Ester. Other detectable labels that can be used include other dyes, fluorophores, chromophores, mass tags, quantum dots and the like and those disclosed in U.S. Pat. No. 6,924,372.

In one embodiment, the established assay range for sample concentration is from 0.4 mg/ml to 0.6 mg/ml, corresponding to a final concentration being analyzed of about 7 µg/ml to 11 µg/ml which is subjected to MCE analysis on a microchip capillary electrophoresis system to produce an electropherogram. In another embodiment, the established assay range for sample concentration is from 0.2 mg/ml to 0.6 mg/ml, corresponding to a final concentration being analyzed of about 3.6 µg/ml to 11 µg/ml which is subjected to MCE analysis on a microchip capillary electrophoresis system to produce an electropherogram. The method concludes by identifying peaks in the electropherogram corresponding to protein drug product, contaminants, and/or impurities.

C. Instrumentation

Instrumentation for conducting the disclosed MCE assays is commercially available. In an embodiment, the disclosed MCE assays are performed using LabChip GXII or LabChip GXII Touch HT and LabChip® HT Protein Express Chip.

III. Proteins of Interest

The protein of interest, for example a protein drug product, assayed with the disclosed MCE assays and reagents can be any protein of interest suitable for expression in prokaryotic or eukaryotic cells and can be used in the engineered host cell systems provided. For example, the protein of interest includes, but is not limited to, an antibody or antigen-binding fragment thereof, a chimeric antibody or antigen-binding fragment thereof, an ScFv or fragment thereof, an Fc-fusion protein or fragment thereof, a growth factor or a fragment thereof, a cytokine or a fragment thereof, or an extracellular domain of a cell surface receptor or a fragment thereof. Proteins of interest may be simple polypeptides consisting of a single subunit, or complex multisubunit proteins comprising two or more subunits. The protein of interest may be a biopharmaceutical product, food additive or preservative, or any protein product subject to purification and quality standards.

In some embodiments, the protein drug product (protein of interest) is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody. In one embodiment, the antibody is a chimeric IgG2/IgG4 antibody. In one embodiment, the antibody is a chimeric IgG2/IgG1 antibody. In one embodiment, the antibody is a chimeric IgG2/IgG1/IgG4 antibody.

Embodiments can be used with any known therapeutic antibody therapeutic. In some embodiments, the antibody can be selected from the group consisting of an anti-Programmed Cell Death 1 antibody (e.g. an anti-PD1 antibody as described in U.S. Pat. Appln. Pub. No. US2015/0203579A1), an anti-Programmed Cell Death Ligand-1 (e.g., an anti-PD-L1 antibody as described in in U.S. Pat. Appln. Pub. No. US2015/0203580A1), an anti-D114 antibody, an anti-Angiopoetin-2 antibody (e.g., an anti-ANG2 antibody as described in U.S. Pat. No. 9,402,898), an anti-Angiopoetin-Like 3 antibody (e.g., an anti-AngPtl3 antibody as described in U.S. Pat. No. 9,018,356), an anti-platelet derived growth factor receptor antibody (e.g., an anti-PDGFR antibody as described in U.S. Pat. No. 9,265,827), an anti-Erb3 antibody, an anti-Prolactin Receptor antibody (e.g., anti-PRLR antibody as described in U.S. Pat. No. 9,302,015), an anti-Complement 5 antibody (e.g., an anti-o5 antibody as described in U.S. Pat. Appln. Pub. No US2015/0313194A1), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. Appln. Pub. No. US2015/0259423A1), an anti-Proprotein Convertase Subtilisin Kexin-9 antibody (e.g., an anti-PCSK9 antibody as described in U.S. Pat. No. 8,062,640 or U.S. Pat. No. 9,540,449), an Anti-Growth and Differentiation Factor-8 antibody (e.g. an anti-GDF8 antibody, also known as anti-myostatin antibody, as described in U.S. Pat Nos. 8,871,209 or 9,260,515), an anti-Glucagon Receptor (e.g. anti-GCGR antibody as described in U.S. Pat. Appln. Pub. Nos. US2015/0337045A1 or US2016/0075778A1), an anti-VEGF antibody, an anti-IL1R antibody, an interleukin 4 receptor antibody (e.g., an anti-IL4R antibody as described in U.S. Pat. Appln. Pub. No. US2014/0271681A1 or U.S. Pat Nos. 8,735,095 or 8,945,559), an anti-interleukin 6 receptor antibody (e.g., an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-IL6 antibody, an anti-IL7 antibody, an anti-interleukin 33 (e.g., anti-IL33 antibody as described in U.S. Pat. Nos. 9,453,072 or 9,637,535), an anti-Respiratory syncytial virus antibody (e.g., anti-RSV antibody as described in U.S. Pat. Appln. Pub. No. 9,447,173), an anti-Cluster of differentiation 3 (e.g., an anti-CD3 antibody, as described in U.S. Pat. Nos. 9,447,173 and 9,447,173, and in U.S. Application No. 62/222,605), an anti-Cluster of differentiation 20 (e.g., an anti-CD20 antibody as described in U.S. Pat. Nos. 9,657,102 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel d1 antibody (e.g. as described in U.S. Pat. No. 9,079,948), an anti-Middle East Respiratory Syndrome virus (e.g. an anti-MERS antibody as described in U.S. Pat. Appln. Pub. No. US2015/0337029A1), an anti-Ebola virus antibody (e.g. as described in U.S. Pat. Appln. Pub. No. US2016/0215040), an anti-Zika virus antibody, an anti-Lymphocyte Activation Gene 3 antibody (e.g. an anti-LAG3 antibody, or an anti-CD223 antibody), an anti-Nerve Growth Factor antibody (e.g. an anti- NGF antibody as described in U.S. Pat. Appln. Pub. No. US2016/0017029 and U.S. Pat. Nos. 8,309,088 and 9,353,176) and an anti-Protein Y antibody. In some embodiments, the bispecific antibody can be selected from the group consisting of an anti-CD3×anti-CD20 bispecific antibody (as described in U.S. Pat. Appln. Pub. Nos. US2014/0088295A1 and US20150266966A1), an anti-CD3×anti-Mucin 16 bispecific antibody (e.g., an anti-CD3×anti-Muc16 bispecific antibody), and an anti-CD3×anti-Prostate-specific membrane antigen bispecific antibody (e.g., an anti-CD3×anti-PSMA bispecific antibody). In some embodiments, the protein of interest can be selected from the group consisting of casirivimab, imdevimab, ravulizumab-cwvz, abciximab, adalimumab, adalimumab-atto, ado-trastuzumab, alemtuzumab, alirocumab, atezolizumab, avelumab, basiliximab, belimumab, benralizumab, bevacizumab, bezlotoxumab, blinatumomab, brentuximab vedotin, brodalumab, canakinumab, capromab pendetide, certolizumab pegol, cemiplimab, cetuximab, denosumab, dinutuximab, dupilumab, durvalumab, eculizumab, elotuzumab, emicizumab-kxwh, emtansinealirocumab, evinacumab, evolocumab, fasinumab, golimumab, guselkumab, ibritumomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxibacumab, reslizumab, rinucumab, rituximab, sarilumab, secukinumab, siltuximab, tocilizumab, tocilizumab, trastuzumab, trevogrumab, ustekinumab, and vedolizumab.

In some embodiments, the protein of interest is a recombinant protein that contains an Fc moiety and another domain, (e.g., an Fc-fusion protein). In some embodiments, an Fc-fusion protein is a receptor Fc-fusion protein, which contains one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a TRAP protein, such as an IL-1 trap (e.g., rilonacept, which contains the IL-1RAcP ligand binding region fused to the Il-1R1 extracellular region fused to Fc of hIgG1; see U.S. Pat. No. 6,927,044, or a VEGF trap (e.g., aflibercept or ziv-aflibercept, which comprises the Ig domain 2 of the VEGF receptor Flt1 fused to the Ig domain 3 of the VEGF receptor Flk1 fused to Fc of hIgG1; see U.S. Pat. Nos. 7,087,411 and 7,279,159). In other embodiments, an Fc-fusion protein is a ScFv-Fc-fusion protein, which contains one or more of one or more antigen-binding domain(s), such as a variable heavy chain fragment and a variable light chain fragment, of an antibody coupled to an Fc moiety.

IV. Cell Culture

The protein drug product assayed with the disclosed MCE assays and reagents are produced cell cultures. The cell cultures can be a "fed-batch cell culture" or "fed-batch culture" which refers to a batch culture wherein the cells and culture medium are supplied to the culturing vessel initially and additional culture nutrients are slowly fed, in discrete increments, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" whereas all components for cell culturing (including the animal cells and all culture nutrients) are supplied to the culturing vessel at the start of the culturing process in batch culture. Fed-batch culture may be different from "perfusion culture" insofar as the supernatant is not removed from the culturing vessel during a standard fed-batch process, whereas in perfusion culturing, the cells are restrained in the culture by, e.g., filtration, and the culture medium is continuously or intermittently introduced and removed from the culturing vessel. However, removal of samples for testing purposes during fed-batch cell culture is contemplated. The fed-batch process continues until it is determined that maximum working volume and/or protein production is reached, and protein is subsequently harvested.

The cell culture can be a "continuous cell culture" which is a technique used to grow cells continually, usually in a particular growth phase. For example, if a constant supply of cells is required, or the production of a particular protein of interest is required, the cell culture may require maintenance in a particular phase of growth. Thus, the conditions must be continually monitored and adjusted accordingly in order to maintain the cells in that particular phase.

The cells are cultured in cell culture medium. The terms "cell culture medium" and "culture medium" refer to a nutrient solution used for growing mammalian cells that typically provides the necessary nutrients to enhance growth of the cells, such as a carbohydrate energy source, essential (e.g., phenylalanine, valine, threonine, tryptophan, methionine, leucine, isoleucine, lysine, and histidine) and nonessential (e.g., alanine, asparagine, aspartic acid, cysteine, glutamic acid, glutamine, glycine, proline, serine, and tyrosine) amino acids, trace elements, energy sources, lipids, vitamins, etc. Cell culture medium may contain extracts, e.g., serum or peptones (hydrolysates), which supply raw materials that support cell growth. Media may contain yeast-derived or soy extracts, instead of animal-derived extracts. Chemically defined medium refers to a cell culture medium in which all of the chemical components are known (i.e., have a known chemical structure). Chemically defined medium is entirely free of animal-derived components, such as serum- or animal-derived peptones. In one embodiment, the medium is a chemically defined medium.

The solution may also contain components that enhance growth and/or survival above the minimal rate, including hormones and growth factors. The solution may be formulated to a pH and salt concentration optimal for survival and proliferation of the particular cell being cultured.

A "cell line" refers to a cell or cells that are derived from a particular lineage through serial passaging or subculturing of cells. The term "cells" is used interchangeably with "cell population".

The term "cell" includes any cell that is suitable for expressing a recombinant nucleic acid sequence. Cells include those of prokaryotes and eukaryotes, such as bacterial cells, mammalian cells, human cells, non-human animal cells, avian cells, insect cells, yeast cells, or cell fusions such as, for example, hybridomas or quadromas. In certain embodiments, the cell is a human, monkey, ape, hamster, rat or mouse cell. In other embodiments, the cell can be selected from the following cells: Chinese Hamster Ovary (CHO) (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK21), HeLa, HepG2, WI38, MRC 5, Colo25, HB 8065, HL-60, lymphocyte, e.g., Jurkat (T lymphocyte) or Daudi (B lymphocyte), A431

(epidermal), U937, 3T3, L cell, C127 cell, SP2/0, NS-0, MMT cell, stem cell, tumor cell, and a cell line derived from an aforementioned cell. In some embodiments, the cell comprises one or more viral genes, e.g., a retinal cell that expresses a viral gene (e.g., a PER.C6® cell). In some embodiments, the cell is a CHO cell. In other embodiments, the cell is a CHO K1 cell.

V. Kits

One embodiment provides a kit including the one or more of the disclosed buffers or ingredients to make the disclosed buffers. The kit can include a container for the buffers or ingredients. The buffers can be in solution or in lyophilized form. The kit optionally also includes a second container containing a diluent or reconstituting solution for the lyophilized formulation; and optionally, instructions for the use of the solution or the reconstitution and/or use of the lyophilized buffers or powdered ingredients.

The kit may further include additional reagents needed to perform the disclosed MCE assays including one or more of a buffer, a diluent, and a filter. The buffer and reagents can be in a bottle, a vial, or test tube.

The following examples are not intended to limit the scope of what the inventors regard as their inventions.

EXAMPLES

Example 1

MCE Assay for Purity and Impurity Analysis of Therapeutic Proteins

Methods and Materials:
Materials:
LabChip GXII or LabChip GXII Touch HT and LabChip® HT Protein Express Chip were used for capillary electrophoretic separation and data collection (Perkin Elmer). Non-reducing and reducing denaturing buffers disclosed above were used for the MCE assay.
Methods:
Microchip Capillary Electrophoresis (MCE) provides analysis of protein purity and impurities suitable for in-process testing, lot release, and stability indication. Protein samples of casirivimab and imdevimab were prepared by denaturing the sample through heating and addition of lithium dodecyl sulfate (LDS) with either an alkylating (non-reduced) or reducing agent (reduced). The resulting samples were then incubated with an amine ester dye to covalently label any free amine groups. Labeled samples were injected onto a microchip where the application of a current separated the sample components according to size (from low to high molecular weight). Detection was performed by laser-induced fluorescence, producing an electropherogram. Analysis of the electropherogram provided the relative purity of the sample compared to the impurities present.

Table 1 shows the workflow procedure for preparing a sample for a first MCE assay. Briefly, protein samples were diluted to 0.5 mg/ml. 1 µl of either non-reducing (NR) or reducing (R) denaturing buffer and 4 µl of the diluted sample were added to a 96-well plate. The sample was mixed, centrifuged, and heated for 10 minutes at the temperature specified for the product, typically 75° C. The samples were then labeled with 5 µM commercially available dye (for example Dyomics DY-631 NHS Ester, also called PICO dye). The samples were mixed, centrifuged, and then heated at 35° C. for 30 minutes. The labeled sample was then diluted with 105 µl of dilute stop solution. The samples were separated using LabChip GXII or LabChip GXII Touch HT.

TABLE 1

Sample preparation method for a first MCE assay.

| Sample Preparation | |
| --- | --- |
| NR | R |
| 4 µl 0.5 mg/mL Sample | 4 µl 0.5 mg/mL Sample |
| 1 µL NR Buffer | 1 µL R Buffer |
| Mix, centrifuge, heat at Specified Temperature for 10 minutes | |

| Sample Labeling |
| --- |
| 5 µL Denatured Sample |
| 5 µL 5 µM PICO dye |
| Mix, centrifuge, heat at 35° C. for 30 minutes |

| Final Dilution |
| --- |
| 5 µL Labeled Sample |
| 105 µL Dilute Stop Solution |

| Separation Method |
| --- |
| HT PICO Protein Express 200 |

Table 2 shows the workflow procedure for preparing a sample for a second MCE assay. Briefly, protein samples were diluted to 0.5 or 2 mg/ml. 10 µl of either non-reducing (NR) or reducing (R) denaturing buffer and 40 µl of the diluted sample were added to a 96-well plate. The sample was mixed, centrifuged, and heated for 10 minutes at the temperature specified for the product, typically 60° C. The samples were then labeled with 16 µM commercially available dye (for example Dyomics DY-631 NHS Ester). The samples were mixed, centrifuged, and then heated at 35° C. for 15 minutes. The labeled sample was then diluted with 105 µl of dilute stop solution or dilute solution. The samples were separated using LabChip GXII or LabChip GXII Touch HT.

Example 1A

Non-Reducing Buffer

The general preparation presented in Table 1 was followed, using in the Sample Preparation Step a non-reducing aqueous electrophoresis sample buffer that contained 166 mM 2-iodoacetamide, 0.81% lithium dodecyl sulfate, and 81 mM sodium phosphate and had a pH of 6. The sample was heated at 75_° C. for 10 minutes. The Sample Labeling step used 5 µM dye solution. The Final Dilution step used 105 µL Dilute Stop Solution.

Example 1B

Reducing Buffer

The general preparation presented in Table 1 was followed, using in the Sample Preparation Step a reducing aqueous electrophoresis sample buffer that contained 0.69% lithium dodecyl sulfate, 69 mM sodium phosphate, and 142 mM dithiothreitol, and had a pH of 9. The sample was heated at 75° C. for 10 minutes. The Sample Labeling step used 5 µM dye solution. The Final Dilution step used 105 µL Dilute Stop Solution.

TABLE 2

General sample preparation method for a second MCE assay.

| Sample Preparation | |
|---|---|
| NR | R |
| 40 µl 0.2 mg/mL Sample | 40 µl 0.2 mg/mL Sample |
| 10 µL NR Buffer | 10 µL R Buffer |
| Mix, centrifuge, heat at Specified Temperature for 10 minutes | |

| Sample Labeling |
|---|
| 5 µL Denatured Sample |
| 16 µL 16 µM PICO dye |
| Mix, centrifuge, heat at 35° C. for 15 minutes |

| Final Dilution |
|---|
| 5 µL Labeled Sample |
| 105 µL Dilute Stop Solution or Dilute Solution |

| Separation Method |
|---|
| HT PICO Protein Express 200 |

Buffers

Stock solutions of 200 mM Sodium Phosphate Monobasic Monohydrate, 200 mM Sodium Phosphate Dibasic Hepathydrate, and 10% Lithium Dodecyl Sulfate (LDS) were prepared. Alternately, a commercially prepared sodium phosphate buffer with a pH of 8 was used.

Using the stock solutions and Milli-Q® water, solutions of 100 mM Sodium Phosphate 1% LDS pH 6 and 100 mM Sodium Phosphate 1% LDS pH 9 were prepared.

Alternate buffers were made using stock solutions and Milli-Q water include solutions of 100 mM Sodium Phosphate 2% LDS pH 6 and 100 mM Sodium Phosphate 2% LDS pH 8.

A non-reducing buffer was prepared by adding 34 µL 1M Iodoacetamide (IAM) (prepared fresh in Milli-Q® water)+166 µL 100 mM Sodium Phosphate 1% LDS pH 6+5 µL Milli-Q® water. The final concentrations were 166 mM 2-iodoacetamide, 0.81% lithium dodecyl sulfate, and 81 mM Sodium phosphate.

An alternate non-reducing buffer was prepared by adding 800 µL 1M Iodoacetamide (IAM) (prepared fresh in Milli-Q® water)+1200 µL 100 mM Sodium Phosphate 2% LDS pH 8. The final concentrations were 200 mM 2-iodoacetamide, 1.2% lithium dodecyl sulfate, and 60 mM Sodium phosphate.

Yet another non-reducing buffer was prepared by adding 800 µL 1M Iodoacetamide (IAM) (prepared fresh in Milli-Q® water)+1200 µL 100 mM Sodium Phosphate 2% LDS pH 6. The final concentrations were 200 mM 2-iodoacetamide, 1.2% lithium dodecyl sulfate, and 60 mM Sodium phosphate.

A reducing buffer was prepared by adding 68 µL 10× Reducing agent (500 mM dithiothreitol (DTT)+166 µL 100 mM Sodium Phosphate 1% LDS pH 9+6 µL Milli-Q® water. The final concentrations were 0.69% lithium dodecyl sulfate; 69 mM sodium phosphate, and 142 mM dithiothreitol.

An alternate reducing buffer was prepared by adding 320 µL 10× Reducing agent (500 mM dithiothreitol (DTT)+1200 µL 100 mM Sodium Phosphate 2% LDS pH 8+480 µL Milli-Q® water. The final concentrations were 1.2% lithium dodecyl sulfate; 60 mM sodium phosphate, and 80 mM dithiothreitol.

Example 2A

Non-Reducing Buffer

The general preparation presented in Table 2 was followed, using in the Sample Preparation Step a non-reducing aqueous electrophoresis sample buffer that contained 200 mM 2-iodoacetamide, 1.2% lithium dodecyl sulfate, and 60 mM sodium phosphate and had a pH of 8. The sample was heated at 60° C. for 10 minutes. The Sample Labeling step used 16 µM dye solution. The Final Dilution step used 105 µL Dilute Stop Solution.

Example 2B

Reducing Buffer

The general preparation presented in Table 2 was followed, using in the Sample Preparation Step a reducing aqueous electrophoresis sample buffer that contained 1.2% lithium dodecyl sulfate, 60 mM sodium phosphate, and 80 mM dithiothreitol, and had a pH of 8. The sample was heated at 60° C. for 10 minutes. The Sample Labeling step used 16 µM dye solution. The Final Dilution step used 105 µL Dilute Stop Solution.

Example 2C

Non-Reducing Buffer, Non-Quenching

The general preparation presented in Table 2 was followed, using in the Sample Preparation Step a non-reducing aqueous electrophoresis sample buffer that contained 200 mM 2-iodoacetamide, 1.2% lithium dodecyl sulfate, and 60 mM sodium phosphate and had a pH of 6. The sample was heated at 63° C. for 10 minutes. The Sample Labeling step used 16 µM dye solution. The Final Dilution step used 105 µL Dilute Solution.

Example 2D

Reducing Buffer, Non-Quenching

The general preparation presented in Table 2 was followed, using in the Sample Preparation Step a reducing aqueous electrophoresis sample buffer that contained 1.2% lithium dodecyl sulfate, 60 mM sodium phosphate, and 80 mM dithiothreitol, and had a pH of 8. The sample was heated at 63° C. for 10 minutes. The Sample Labeling step used 16 µM dye solution. The Final Dilution step used 105 µL Dilute Solution.

Figure 1B:
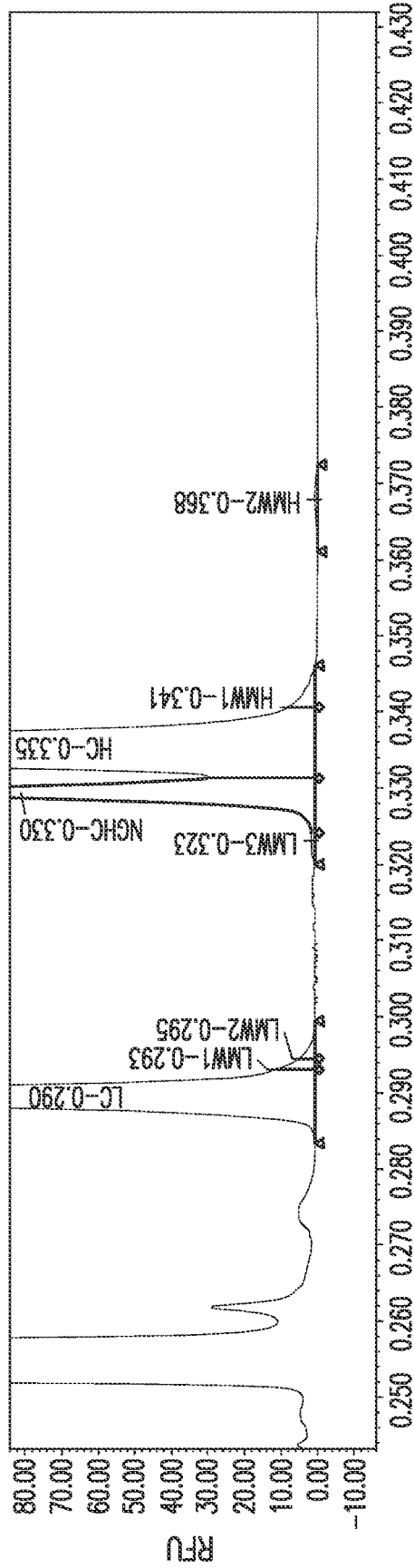
FIG. 1B shows an electropherogram of a typical reduced sample analysis. The X-axis represents time in minutes, and the Y-axis represents the relative fluorescence units (RFU). Increased migration time corresponds to increased protein size.

Results:

Microchip Capillary Electrophoresis (MCE) allows for dramatically reduced sample analysis times, while maintaining the performance and reproducibility standards required for QC analysis. An MCE assay was developed using the non-reduced and reduced denaturing buffers disclosed herein. FIGS. 1A-1B show representative electropherograms of protein in non-reduced samples and reduced samples from the first MCE assay. FIG. 1A shows a non-reduced analysis electropherogram. The main peak (MP) at 0.426 corresponds to the main antibody, and the labeled low molecular weight (LMW) peaks corresponds to antibody fragments. Although not present in this example, in some instances a peak corresponding to one or more high molecular weight fragments are present. FIG. 1B shows a reduced analysis electropherogram. Peaks corresponding to light chain (LC), heavy chain, and non-glycosylated heavy chain (NGHC), low molecular weight (LMW), and high molecular weight (HMW) antibody fragments are labeled accordingly. It should be noted that different products may have variation in the electropherograms produced, and therefore different labeling conventions.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof and, accordingly, reference should be made to the appended claims, rather than to the foregoing specification, as indicating the scope of the invention.

We claim:

1. An aqueous microchip capillary electrophoresis sample buffer for a protein drug sample, the buffer comprising:
   155 to 200 mM 2-iodoacetamide;
   0.50 to 1.5% lithium dodecyl sulfate; and
   60 to 95 mM sodium phosphate,
   wherein the aqueous microchip capillary electrophoresis sample buffer has a pH of less than or equal to 8, and wherein microchip capillary electrophoresis is used to identify contaminants in the protein drug sample.

2. The aqueous microchip capillary electrophoresis sample buffer of claim 1, wherein the pH is 6.

3. The aqueous microchip capillary electrophoresis sample buffer of claim 1, comprising 200 mM 2-iodoacetamide, 1.2% lithium dodecyl sulfate, and 60 mM sodium phosphate.

4. A method for identifying contaminants or impurities in a protein drug sample, the method comprising the steps of:
   adding the protein drug sample to the buffer of claim 1 to form a buffered protein drug sample;
   heating the buffered protein drug sample to 45 to 75° C. for 5 to 15 minutes to form a denatured buffered protein drug sample;
   adding a detectable label to the denatured buffered protein drug sample and heating it at 30 to 40° C. for 10 to 40 minutes to form a denatured labeled protein drug sample;
   diluting the denatured labeled protein drug sample and subjecting it to microchip capillary electrophoresis (MCE) to separate the diluted protein drug sample on a microchip capillary electrophoresis system to produce an electropherogram; and
   identifying peaks in the electropherogram corresponding to the protein drug, contaminants, and/or impurities.

5. The method of claim 4, wherein the buffered protein drug sample is heated at 60° C. for 10 min.

6. The method of claim 4, wherein the labeled protein drug sample is heated at 35° C. for 15 minutes.

7. The method of claim 4, wherein the diluted protein drug sample is 3.6 µg/ml.

8. A kit comprising the buffer according to claim 1, and written instructions for preparing a sample for electrophoresis in the buffer.

9. An aqueous microchip capillary electrophoresis sample buffer for a protein drug sample, the buffer comprising:
   165.9 mM 2-iodoacetamide,
   0.81% lithium dodecyl sulfate, and
   81 mM Sodium phosphate,
   wherein the aqueous microchip capillary electrophoresis sample buffer has a pH of 6.0, and
   wherein microchip capillary electrophoresis is used to identify contaminants in the protein drug sample.

10. An aqueous microchip capillary electrophoresis sample buffer for a protein drug sample, the buffer comprising:
    200 mM 2-iodoacetamide,
    1.2% lithium dodecyl sulfate, and
    60 mM Sodium phosphate,
    wherein the aqueous microchip capillary electrophoresis sample buffer has a pH of 8.0, and
    wherein microchip capillary electrophoresis is used to identify contaminants in the protein drug sample.

11. An aqueous microchip capillary electrophoresis sample buffer for a protein drug sample, the buffer consisting of:
    0.50 to 1.5% lithium dodecyl sulfate,
    45 to 75 mM sodium phosphate, and
    80 to 155 mM dithiothreitol,
    wherein the aqueous microchip capillary electrophoresis sample buffer has a pH of 8 or greater, and wherein microchip capillary electrophoresis is used to identify contaminants in the protein drug sample.

12. The aqueous microchip capillary electrophoresis sample buffer of claim 11, wherein the pH is 8.

13. The aqueous microchip capillary electrophoresis sample buffer of claim 12, comprising 80 mM dithiothreitol.

14. The aqueous microchip capillary electrophoresis sample buffer of claim 12, comprising 142 mM dithiothreitol.

15. The aqueous microchip capillary electrophoresis sample buffer of claim 11, wherein the pH is 9.

16. The aqueous microchip capillary electrophoresis sample buffer of claim 11, consisting of 1.2% lithium dodecyl sulfate and 60 mM sodium phosphate.

17. An aqueous microchip capillary electrophoresis sample buffer for a protein drug sample, the buffer consisting of:
    0.69% lithium dodecyl sulfate,
    69 mM sodium phosphate, and
    80 to 155 mM dithiothreitol,
    wherein the aqueous microchip capillary electrophoresis sample buffer has a pH of 9.0, and
    wherein microchip capillary electrophoresis is used to identify contaminants in the protein drug sample.

18. An aqueous microchip capillary electrophoresis sample buffer for a protein drug sample, the buffer consisting of:
    1.2% lithium dodecyl sulfate,
    60 mM sodium phosphate, and
    80 mM dithiothreitol,
    wherein the aqueous microchip capillary electrophoresis sample buffer has a pH of 8.0, and
    wherein microchip capillary electrophoresis is used to identify contaminants in the protein drug sample.

19. A method for identifying contaminants or impurities in a protein drug sample, the method comprising the steps of:
    adding a protein sample to a buffer to form a buffered protein drug sample;
    heating the buffered protein drug sample to 45 to 75° C. for 5 to 15 minutes to form a denatured protein drug sample, wherein the buffer comprises 200 mM 2-iodoacetamide, 1.2% lithium dodecyl sulfate, and 60 mM sodium phosphate at a pH of 6.0;

adding a detectable label to the denatured protein drug sample and heating it at 30 to 40° C. for 10 to 40 minutes to form a denatured labeled protein drug sample;

diluting the denatured labeled protein drug sample and subjecting it to microchip capillary electrophoresis (MCE) analysis on a microchip capillary electrophoresis system to produce an electropherogram; and identifying peaks in the electropherogram corresponding to contaminants or impurities.

20. The method of claim 19, wherein the buffered protein drug sample is heated at 60° C. for 10 min.

21. The method of claim 19, wherein the sample is heated at 35° C. for 15 minutes.

22. The method of claim 19, wherein the diluted protein drug sample is 3.6 µg/ml.

23. The method of claim 19, wherein the detectable label is DY-631 N-hydroxysuccinimidyl ester.

24. The method of claim 19, wherein the detectable label is reconstituted with dimethyl sulfoxide (DMSO) followed by dilution with 200 mM Sodium Phosphate pH 7.2 buffer.

* * * * *